United States Patent [19]

Nardi

[11] Patent Number: 5,221,206
[45] Date of Patent: Jun. 22, 1993

[54] DEVICE FOR PRODUCING QUICK COUPLINGS FOR DENTAL PROSTHESES

[75] Inventor: Ezio Nardi, Bologna, Italy

[73] Assignee: Rhein 82 S.n.c. di Nardi Ezio & C., Bologna, Italy

[21] Appl. No.: 883,435

[22] Filed: May 15, 1992

[30] Foreign Application Priority Data

May 24, 1991 [IT] Italy .............. B091U-000103[U]

[51] Int. Cl.⁵ ............................................. A61C 13/225
[52] U.S. Cl. ...................... 433/193; 433/181; 433/194
[58] Field of Search .......... 433/172, 193, 194, 181, 433/182, 173, 196, 169, 220

[56] References Cited

U.S. PATENT DOCUMENTS

| | | | |
|---|---|---|---|
| 1,889,756 | 12/1932 | McNamhra | 433/193 |
| 2,002,048 | 5/1935 | Thomas | 433/172 |
| 2,151,723 | 3/1939 | Trinkle | 437/172 |
| 2,672,686 | 3/1954 | Herzberg | 433/172 |
| 3,473,222 | 10/1969 | Kesler | 433/173 |
| 4,966,553 | 10/1990 | Sandhaus | 433/181 |
| 5,030,094 | 7/1991 | Nardi et al. | 433/181 |
| 5,133,662 | 7/1992 | Metcalfe | 433/172 |

Primary Examiner—Paul J. Hirsch
Attorney, Agent, or Firm—Guido Modiano; Albert Josif

[57] ABSTRACT

Device for producing quick couplings for dental prostheses, of the type which includes at least one substantially spherical male element, which is intended to be monolithically integrated with a fixed part of the prosthesis, and a female element, whose inner shape is complementary to the shape of the male element, which is correspondingly provided on a removable part of said prosthesis, includes a pair of auxiliary bars, made of a calcinable plastic material, which are connectable one on top of the other, and which cooperate so as to define at least one compartment whose shape is complementary to the outside shape of a cap which defines the female element, the bars being arrangeable about the male element in order to obtain a model of a metallic piece of the removable part of the prosthesis to be produced by lost-wax casting.

4 Claims, 1 Drawing Sheet

DEVICE FOR PRODUCING QUICK COUPLINGS FOR DENTAL PROSTHESES

BACKGROUND OF THE INVENTION

The present invention relates to a device for producing quick couplings for dental prostheses.

Removable dental prostheses are currently known which have appropriate couplings for rapid anchoring to the remaining dental structures. Conventional couplings often have grip problems and tend to slacken in the course of time, creating many problems to their users. Furthermore, said couplings are often relatively expensive, so that their replacement is scarcely convenient.

In order to obviate this problem, a quick coupling for dental prostheses has been proposed which is capable of assuring durable grip, as described in U.S. Pat. No. 5,030,094.

Said quick coupling for dental prostheses essentially comprises at least one spherical male element, which is intended to be integrated in a fixed part of the prosthesis, and a female element, whose shape is complementary to the shape of said male element, correspondingly provided on a removable part of the prosthesis. The female element, which is intended to couple to said male element, is shaped like a cap made of plastic material which is intended to be accommodated and stably retained in the removable part of the prosthesis.

Conveniently, the seat for said plastic cap, in the removable part of the prosthesis, is defined in a metallic piece which is intended to be monolithic with said removable part. Said metallic piece is preferably obtained by lost-wax casting starting from a refractory-lined model of the arch to be reconstructed.

The male element, which is monolithic with the fixed part of the prosthesis, is instead obtained by casting starting from a corresponding prefabricated male element made of calcinable plastic material.

In practice, in order to produce the quick coupling, a metallic element, having the same outside contour as said plastic cap, is applied on the male element. The impression of the unit thus formed is then made, and a model made of refractory material is then produced and subsequently modeled in wax according to the required shape of said metallic piece which is intended to define the seat of the plastic cap. The metallic portion of the removable part of the prosthesis is finally produced by lost-wax casting.

This productive solution is quite obviously rather complicated and expensive, in terms of both work time and materials, since in practice it requires the execution of a duplicate, made of refractory material, of the piece to be modeled.

SUMMARY OF THE INVENTION

A principal aim of the present invention is to solve the above described problem by providing a device which allows to produce couplings for dental prostheses in a simple and rapid manner.

Within the scope of this aim, a further object of the present invention is to provide a device for producing quick couplings for dental prostheses which is simple in concept, safely reliable in operation, and versatile in use.

This aim and this object are both achieved, according to the invention, by the present device for producing quick couplings for dental prostheses, of the type which comprises at least one substantially spherical male element, which is intended to be monolithically integrated with a fixed part of said prosthesis, and a female element, whose inner shape is complementary to the shape of said male element, which is correspondingly provided on a removable part of said prosthesis, characterized in that it comprises a pair of auxiliary bars, made of a calcinable plastic material, which are connectable one on top of the other, and which cooperate so as to define at least one compartment whose shape is complementary to the outside shape of a cap which defines said female element, said bars being arrangeable about said male element in order to obtain a model of a metallic piece of said removable part of the prosthesis to be produced by lost-wax casting.

BRIEF DESCRIPTION OF THE DRAWINGS

The details of the invention will become apparent from the detailed description of a preferred embodiment of the device for producing quick couplings for dental prostheses, illustrated only by way of non-limitative example in the accompanying drawings, wherein.

DESCRIPTION OF THE PREFERRED EMBODIMENTS

Figure 1:
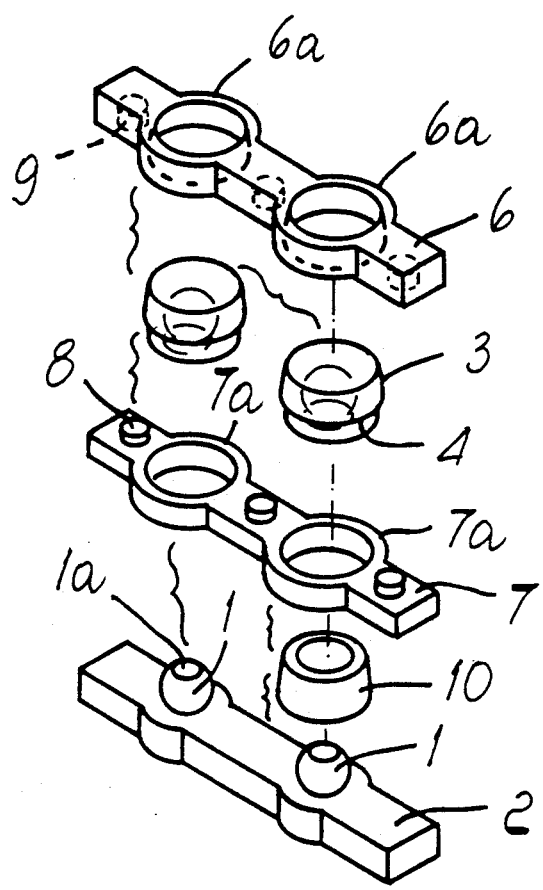
FIG. 1 is an exploded perspective view of the device, according to the invention, for producing quick couplings for dental prostheses.

With particular reference to the above figures, the reference numeral 1 designates a substantially spherical male element of the quick coupling for dental prostheses; said spherical element has two diametrically opposite flat portions 1a, one of which constitutes the base for connecting said male element to the piece which supports it.

In FIG. 1, said supporting piece is constituted, by way of example, by a bar 2 which is suitable for connecting so-called piers and is provided with two male elements 1; in practice, said bar can have various extensions, and may have a single element 1, in order to provide one extracoronal coupling, or more than one element.

The male element 1 is intended to be integrated with a fixed part of the dental prosthesis and to protrude from a uletic region thereof.

The coupling furthermore comprises a female element whose shape is complementary to the shape of a corresponding male element 1 with which it is intended to couple. The female element is arranged in the uletic portion of a removable part of the prosthesis.

Said female element is shaped like a cap 3 made of plastic material which is intended to be accommodated and stably retained in the removable part of the prosthesis. In practice, in fact, the plastic cap 3 is externally provided with a shoulder 4, and the corresponding seat of the prosthesis is shaped complementary to its outer surface.

Preferably, the seat for accommodating and stably retaining the plastic cap 3 is defined in a metallic piece, in practice a sort of cap 5, whose internal surface is shaped complementary to the outer surface of the plastic cap 3. Conveniently, the plastic cap 3 tapers starting from the shoulder 4, so as to facilitate insertion in the metallic cap 5 in which it then couples in a snaptogether manner without the possibility of disengaging without destroying it.

A device which comprises a pair of auxiliary bars 6 and 7, which are made of calcinable plastic material and are suitable for being coupled one on top of the other, is used in order to produce the quick coupling, according to the present invention.

The bars 6 and 7 define, in corresponding positions, at least one respective annular portion 6a and 7a; said annular portions are two in the case shown in FIG. 1 and correspond to the same number of male elements 1 of the bar 2. The annular portions 6a and 7a are suitable for cooperating in order to define, when the two bars 6 and 7 are coupled, a compartment whose shape is complementary to the shape of the plastic cap 3 in which the female element of the coupling is defined. For the sake of greater clarity, the contour defined by said cap 3 is shown in FIG. 1.

In particular, the connecting region of the annular portions 6a and 7a is suitable for defining a shoulder which corresponds to the shoulder 4 of the plastic cap 3.

The bars 6 and 7 are suitable for being coupled by means of a plurality of pivots 8 which protrude from one bar and are intended to enter corresponding holes 9 of the other bar.

The coupled bars 6 and 7 are intended to be associated with the bar 2 of the fixed part of the prosthesis, so as to arrange the related annular portions 6a and 7a about a corresponding male element 1. Preferably, a positioning element 10 is prearranged on the male element 1; said positioning element is constituted by a ring which is appropriately tapered externally and is suitable for being inserted in the compartment defined by the annular portions 6a and 7a for a more precise positioning of the bars 6 and 7.

In practice, according to the various requirements, different portions of said calcinable bars, positioned appropriately, are used. Said bars are then joined by means of wax (or self-polymerizing or photopolymerizing or in any case calcinable synthetic resin), preferably taking care to apply a film of wax so as to also close the top of the compartment defined by the annular portions 6a. A model is thus obtained which, after the removal of the male elements 1 and the extraction of the positioning elements 10, allows to produce, by lost-wax casting, a metallic piece which is intended to be monolithically integrated with the removable part of the prosthesis.

Figure 2:
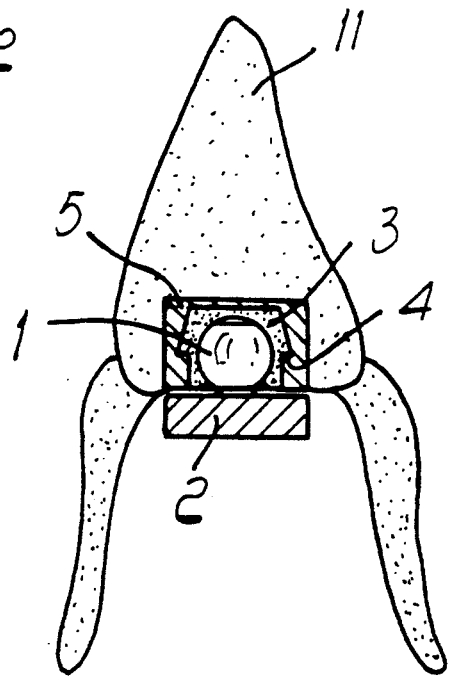
FIG. 2 is a longitudinal sectional view of a prosthesis which uses the coupling thus produced, in its working position.

In FIG. 2, by way of example, said metallic piece defines the cap 5 and is monolithic with the resin of an artificial crown 11 of the removable part of the prosthesis.

It should be noted that said metallic piece can be shaped so as to have, at its base, a pair of longitudinal shoulders suitable for being mounted astride the bar 2 of the fixed part of the prosthesis in order to stably retain the removable part; or, alternatively, it may not have said shoulders in order to allow a certain possibility of oscillation.

The described device allows, in summary, to provide in a simple manner quick couplings for dental prostheses, with an evident saving in time and material. In fact it is not necessary, in this case, to produce a refractory duplicate of the piece to be modeled, but the work is done on the elements which constitute the fixed part of the prosthesis, which are obtained beforehand in a conventional manner, using appropriate portions of the calcinable auxiliary bars.

Said auxiliary bars may furthermore be used individually in order to provide reinforcement elements to be embedded in the removable part of the prosthesis.

In the practical embodiment of the invention, the materials employed, as well as the shape and dimensions, may be any according to the requirements.

I claim:

1. Device for producing quick couplings for dental prosthesis, of the type which comprises at least one substantially spherical male element, which is intended to be monolithically integrated with a fixed part of said prosthesis, and a female element, whose inner shape is complementary to the shape of said male element, which is correspondingly provided on a removable part of said prosthesis, comprising a pair of auxiliary bars, made of a calcinable plastic material, which are connectable one on top of the other, and which cooperate so as to define at least one compartment whose shape is complementary to the outside shape of a cap which defines said female element, said bars being arrangeable about said male element in order to obtain a model of a metallic piece of said removable part of the prosthesis to be produced by lost-wax casting.

2. Device according to claim 1, wherein said auxiliary bars define, in corresponding positions, at least one respective annular portion which is intended to form a related half of said compartment, the connecting region of said annular portions being suitable for defining a shoulder which corresponds to an outside shoulder of said cap.

3. Device according to claim 1, wherein said auxiliary bars are connectable by means of a plurality of pins which protrude from one bar which are insertable in corresponding holes of the other bar.

4. Device according to claim 1, wherein said auxiliary bars are arrangeable about said male element by means of the interposition of a related positioning element which is constituted by a ring which is appropriately tapered on the outside and is suitable for being inserted in said compartment defined by said bars.

* * * * *